United States Patent
Tsagarakis

Patent Number: 5,823,939
Date of Patent: Oct. 20, 1998

[54] EXPANSIBLE PENILE PROSTHESIS

[76] Inventor: Odysseus Tsagarakis, P.O. Box 82, 74 100, Rethymno, Crete, Greece

[21] Appl. No.: 911,562

[22] Filed: Aug. 14, 1997

Related U.S. Application Data

[63] Continuation of Ser. No. 432,511, May 1, 1995, abandoned, Continuation-in-part of Ser. No. 26,824, Mar. 3, 1993, abandoned.

[51] Int. Cl.$^6$ .................................................. A61F 5/00

[52] U.S. Cl. ............................................................. 600/38

[58] Field of Search ................ 600/38–41; 128/842–844

[56] References Cited

U.S. PATENT DOCUMENTS

| | | |
|---|---|---|
| 3,495,589 | 2/1970 | Clement . |
| 4,175,554 | 11/1979 | Gerow . |
| 4,281,648 | 8/1981 | Rogers . |
| 5,046,489 | 9/1991 | Gibson . |

*Primary Examiner*—John P. Lacyk
*Attorney, Agent, or Firm*—Oppenheimer Wolff & Donnelly LLP

[57] ABSTRACT

An inflatable penile prosthesis includes a hollow penis-shaped form and two inflatable elastic tubes over the form. The inflatable tubes are selectively inflated or deflated using hand held air pumps and associated release valves. The hollow form together with the elastic tubes allows the device to be configured for different lengths and widths and to a medium, large, or largest size, or any size therebetween.

9 Claims, 3 Drawing Sheets

EXPANSIBLE PENILE PROSTHESIS

RELATED APPLICATIONS

This is a continuation of U.S. patent application Ser. No. 08/432,511, filed May 1, 1995, now abandoned, which is itself a continuation-in-part of U.S. patent application Ser. No. 08/026,824, filed Mar. 3, 1993 now abandoned. The specifications are incorporated by reference.

BACKGROUND OF THE INVENTION

1. Field of the Invention

The present invention relates to the field of penile prostheses. More particularly, the present invention relates to the field of penile prostheses continuously expandable both circumferentially and longitudinally.

2. Background of the Related Art

Erectile dysfunction in men can be caused by either psychological or organic conditions. See e.g., Sagraves, R. Taylor and Harry W. Schoenberg, Diagnosis and Treatment of Erectile Disturbances, New York (1985). In order to engage in mutually fulfilling sexual relations, a penile prosthesis is often needed. Even when erect, the male sex organ may be inadequate for a number of reasons.

U.S. Pat. No. 3,495,589, issued to Clement, discloses a prosthesis with a flexible, nonelastic sleeve with a means for inflating an inner liner to hold the prosthesis to the male organ. U.S. Pat. No. 4,281,648, issued to Rogers, discloses an inflatable condom that expands at its distal end.

Neither device is capable of expanding both circumferentially and lengthwise to accommodate the needs and desires of the man's sex partner. There exists a need therefore for a penile prosthesis that can be used with an erect or flaccid penis, and that is capable of being expanded both circumferentially and longitudinally to a desired size. erect or flaccid penis, and that is capable of being expanded both circumferentially and longitudinally to a desired size.

SUMMARY OF THE INVENTION

The present invention is an improved penis-like prosthesis which is worn externally and is designed to enhance the sexual relationships of those who depend upon the use of penile prostheses. The prosthesis is capable of expanding and contracting both circumferentially and longitudinally thanks to the invention of two inflatable tubes. It is distinguished by its attached hand pumps and braces, and in the expansion and contraction that give the user the option to reach the desirable size. By inflating and deflating the device as desired, the user can adjust the size of the device for maximum comfort or pleasure during sexual relations.

Because of its ability to change sizes, it is economical.

DETAILED DESCRIPTION OF THE INVENTION

Figure 1:
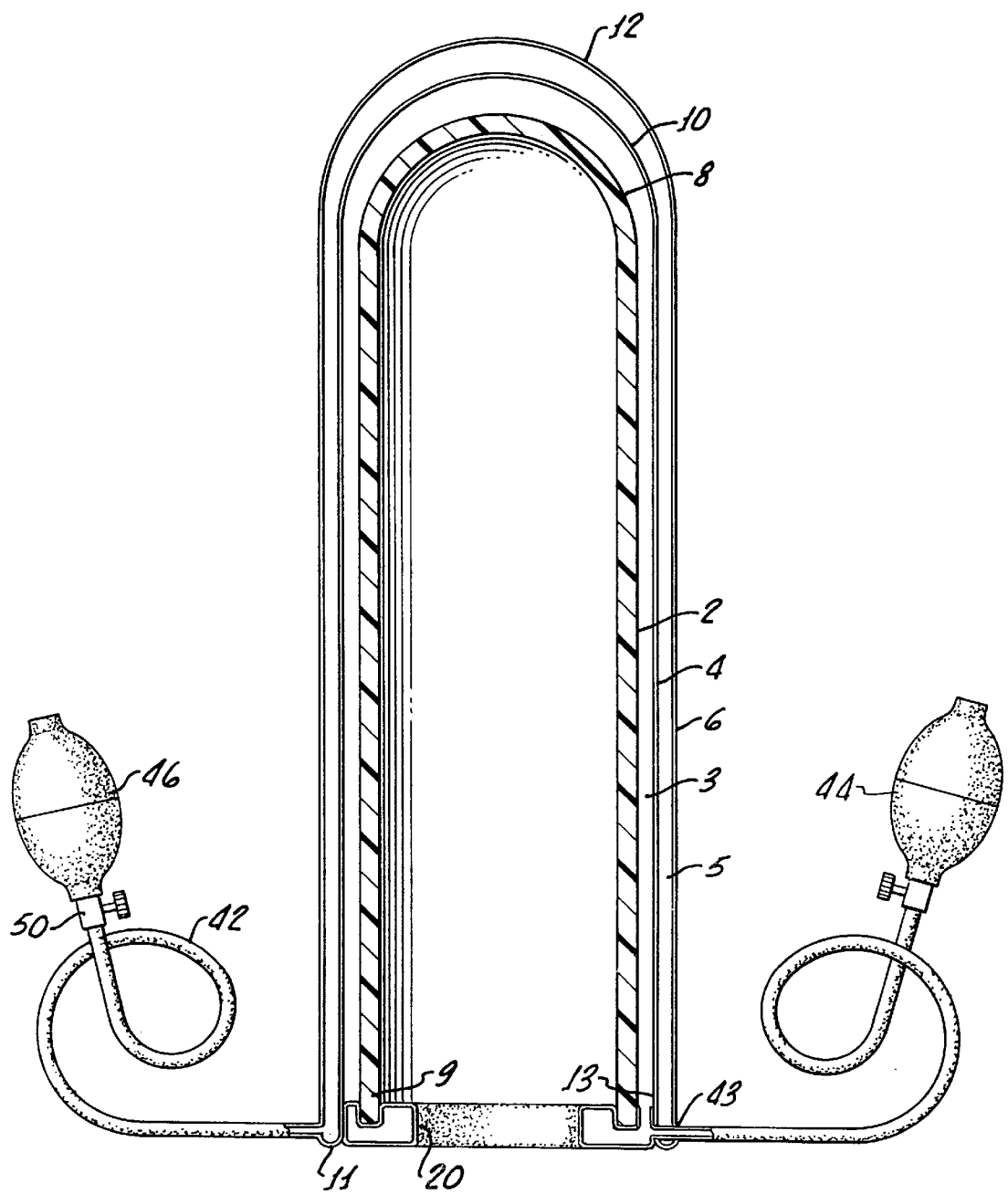
FIG. 1 is a partial sectional view of an exemplary embodiment of the present invention.

Referring to FIG. 1, a penis-shaped hollow form 2 is covered by first elastic tube 4, which, in turn, is covered by a second elastic tube 6. Hollow form 2 is generally cylindrical and may be made of either rigid or semirigid material. Preferably it is 1¾" outside diameter, and 1½" inside diameter and 6⅜" in length. Form 2 has a closed distal end 8 and an open proximal end 9. Elastic tubes 4 and 6 may be made of latex or other inflatable, balloon-like material. Second elastic tube 6 is preferably skin-like in appearance and texture. See FIG. 2. Each elastic tube 4 and 6 has a closed distal end 10, 12 and sealed proximal end 11, 13, respectively.

The first elastic tube 4 is 6⅞" in length and can regularly expand up to about ⅛ around the hollow form 2. Tube 4 expands longitudinally ⅝". The second elastic tube 6 is about 7⅞" in length, and it is capable of expanding to approximately ⅛" around first tube 4. When the second tube expands, it extends about ¾ " beyond the end of first tube 4.

The space between hollow form 2 and first elastic tube 4 forms a first inflation chamber 3. A first air pump 44 inflates first inflation chamber 3 through first inflation tube 40. Similarly, a second air pump 46 inflates a second inflation chamber 5 through a second inflation tube 42. To reach chamber 3, tube 40 passes through a sealed opening in second elastic tube 6 (See FIGS. 1 and 2). Both air pumps 44 and 46 are fitted with air release valves 48 and 50, respectively, for deflating their respective inflation chambers. The inflation tubes 40 and 42 are each about 12" long.

Figure 2:
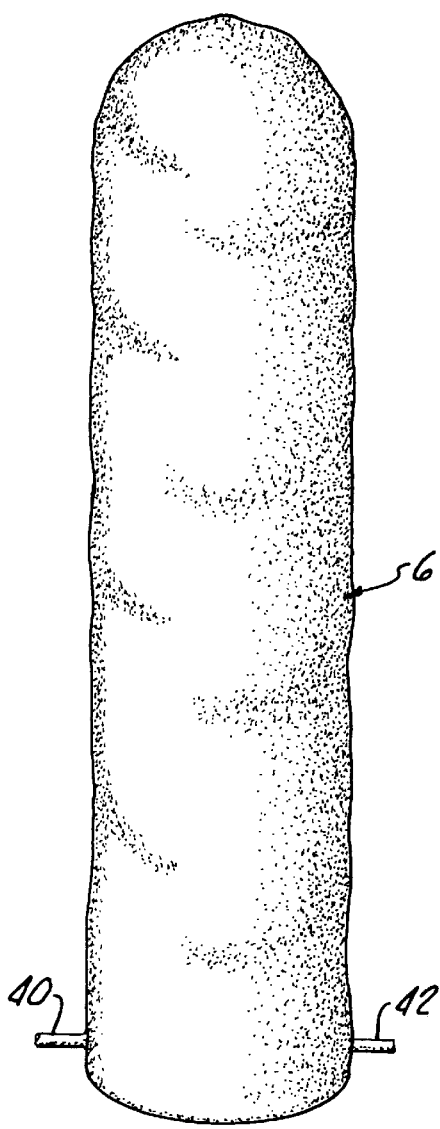
FIG. 2 is a perspective view of a exemplary embodiment of the present invention in its deflated form.

In the uninflated state, elastic tubes 4 and 6 should wrinkle slightly around hollow form 2 (FIG. 2). There will be some build up at the front because of the required expansion in order for the prothesis to reach the fully expanded 7" and 8" lengths.

The present invention contemplates at least three different ways of keeping the device in place. Referring first to FIG. 1, a constricting belt 20 approximately 1" in diameter and ¼" wide of soft texture encircles the base near the proximal end 9 of hollow form 2 and above the proximal ends 11 and 13 of elastic tubes 4 and 6. As FIG. 1 shows, belt 20 communicates with inflation tube 40 and pump 44. When chamber 3 is inflated, belt 20 also inflates.

Figure 3:
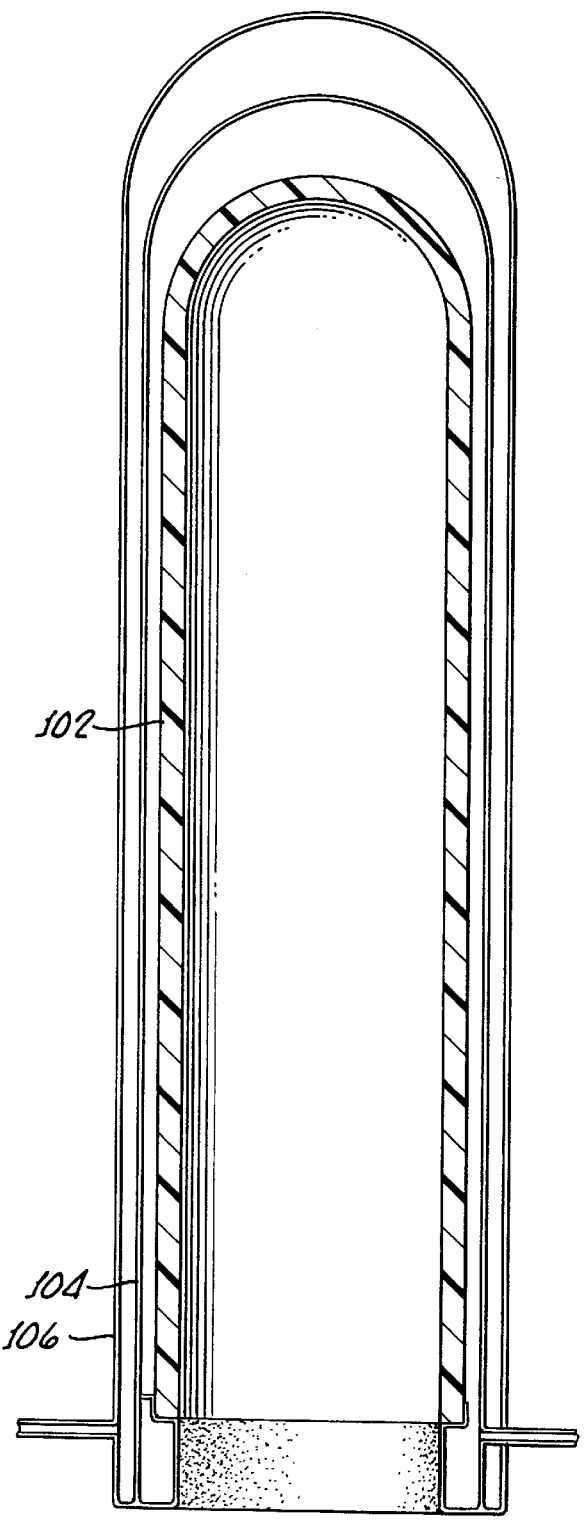
FIG. 3 is a partial sectional view of a second exemplary embodiment of the present invention.
Figure 4:
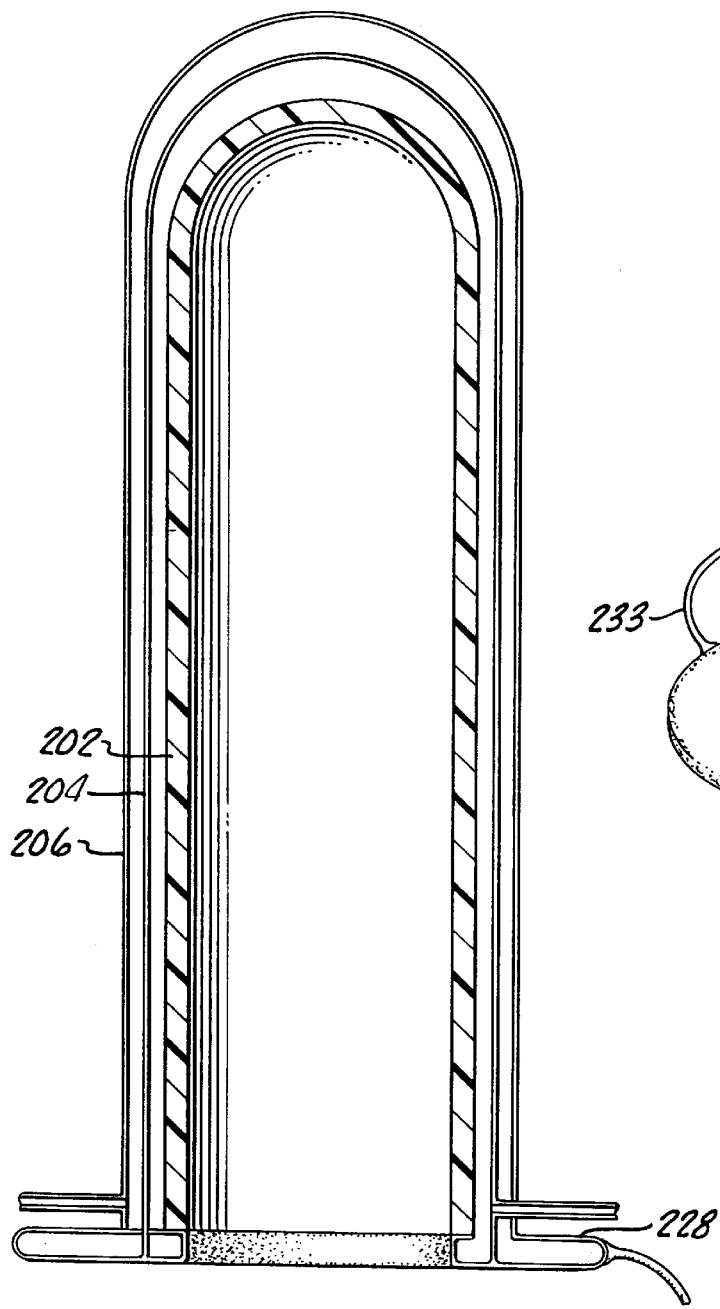
FIG. 4 is a perspective view of a third exemplary embodiment of the present invention in its deflated form.
Figure 5:
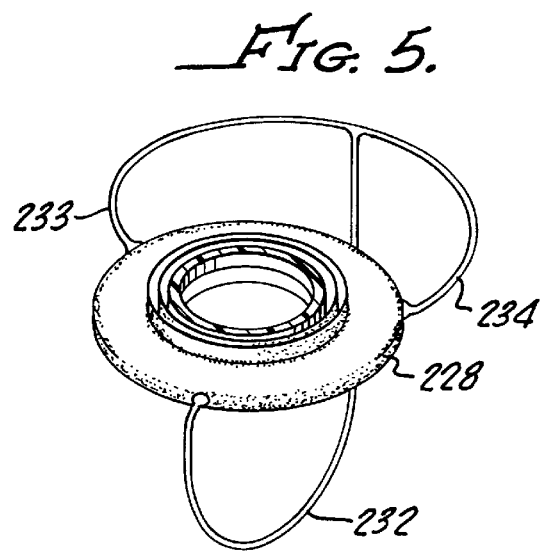
FIG. 5 illustrates a harness that can be used with the present invention.

In another embodiment (FIG. 3), the harder hollow form 102 extends farther proximally. The elastic members 104 and 106 are joined together at 124 proximally of the proximal end 109 of hollow form 102. Then, a wider flared belt In a third embodiment (FIGS. 4 and 5), the inflatable members 204 and 206 flare at base 228. Elastic straps 232, 233 and 234, which can be used for holding the device onto the user, attach to the flared base.

In the device's uninflated state, the device takes on the external dimensions of hollow form 2 (plus the combined thickness of the thin elastic tubes 4 and 6). When first air pump 44 is activated to inflate first inflation chamber 3, the device expands. Simultaneously, constricting belt 20 is activated to secure the device to the base of the penis. First inflation chamber 3 may be inflated and deflated to reach any desired size in the range over which first elastic tube 4 is capable.

When second air pump 46 is activated to inflate second inflation chamber 5, the devices expands still further. Second inflation chamber 5 may also be inflated or deflated to reach any desired size in the range over which second elastic tube 5 is capable. When second inflation chamber 5 is fully inflated, the device reaches its maximum size.

When only pump 44 is activated, the prothesis reaches a size of 2" in diameter and 7" in length. If the user then activates the second air pump 46, the prothesis reaches a larger size, e.g., 2¼" in diameter and 8" in length. The user has the option to inflate elastic tubes 4 and 6 simultaneously or one of them only according to his personal needs and those of his partner.

When the user becomes familiar with the device, he will be able to count the number of squeezes of air pumps 44 and 46 to reach the desired size without having to look.

The device is designed to be long enough to accommodate reservoir-end condoms.

As numerous modifications and alternate embodiments will occur to those skilled in the art, it is intended that the invention is limited only in terms of the appended claims.

I claim:

1. An inflatable penile prosthesis comprising:
   a generally cylindrical form having an open proximal end through which a penis is inserted and a closed distal end;
   a first inflatable cylindrical fluid chamber extending around the form and being closed by a first elastic tube;
   a second inflatable cylindrical fluid chamber disposed outward from said first elastic tube and being closed by a second elastic tube; and
   inflation means attached to the first and second chambers for selectively inflating said first and second inflatable chambers.

2. The inflatable penile prosthesis of claim 1 wherein said second inflatable cylindrical fluid chamber is expandable both circumferentially and longitudinally.

3. The inflatable penile prosthesis of claim 2 wherein said first inflatable cylindrical fluid chamber is expandable both circumferentially and longitudinally.

4. The inflatable penile prosthesis of claim 3 wherein said inflation means comprises at least one air pump.

5. An inflatable penile prosthesis comprising:
   a hollow penis-shaped form comprising a cylinder having a distal end and a proximal end, said form being closed at said distal end and open at said proximal end, said form having an inner surface and an outer surface;
   a first elastic tube concentric with said form and sealed at its proximal end to said proximal end of said form, said first elastic tube being disposed outward from said form, said first elastic tube being closed at its distal end, said form and said first elastic tube defining a first inflation chamber therebetween, said first elastic tube being expandable circumferentially;
   a first inflation tube in fluid communication with said first inflation chamber; and
   a first fluid pump in fluid communication with said first inflation tube.

6. The inflatable penile prosthesis of claim 5 further comprising:
   a second elastic tube concentric with said first elastic tube, said second elastic tube being disposed outward from said first elastic tube, said second elastic tube being closed at its distal end, said proximal end of said second elastic tube being sealingly connected to said proximal end of said first elastic tube, said first and second elastic tubes defining a second inflation chamber therebetween, said second elastic tube being simultaneously expandable both circumferentially and longitudinally;
   a second inflation tube in fluid communication with said second fluid chamber, and
   a second fluid pump in fluid communication with said second inflation pump.

7. The inflatable penile prosthesis of claim 6 further comprising:
   a constricting ring extending around the proximal ends of the first and second elastic tubes.

8. The inflatable penile prosthesis of claim 6 wherein the constricting ring hollow and is in fluid communication with an inflation tube.

9. The inflatable penile prosthesis of claim 5 further comprising:
   a flared base attached to said proximal end of said form, said flared base comprising a substantially cylindrical tube having a proximal end and a distal end, said proximal end of said flared base having a greater diameter than said distal end of said flared base.

* * * * *